United States Patent
Simon et al.

(10) Patent No.: US 8,321,179 B2
(45) Date of Patent: Nov. 27, 2012

(54) MULTIPLE AXES SCANNING SYSTEM AND METHOD FOR MEASURING RADIATION FROM A RADIATION SOURCE

(75) Inventors: William E. Simon, Melbourne, FL (US); Mark Rose, Cocoa, FL (US); Ronald J. Watts, San Antonio, TX (US); Seth Brechbill, Cocoa Beach, FL (US); William Austhof, Melbourne, FL (US); Thomas Allan Simon, Gainesville, FL (US); Jakub Kozelka, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 314 days.

(21) Appl. No.: 12/840,331

(22) Filed: Jul. 21, 2010

(65) Prior Publication Data
US 2011/0022360 A1    Jan. 27, 2011

Related U.S. Application Data

(60) Provisional application No. 61/227,841, filed on Jul. 23, 2009.

(51) Int. Cl.
*G01T 1/00*     (2006.01)
(52) U.S. Cl. ............ 702/189; 702/85; 702/104; 378/65; 378/207; 250/252.1; 250/336.1; 250/388; 250/375
(58) Field of Classification Search .................... 702/85, 702/104, 189; 378/65, 15, 193, 196, 197, 378/18, 19, 207, 205, 5, 210, 4, 164, 165; 250/370.08, 370.09, 252.1, 341.5, 375, 338, 250/370.07, 368, 336.1, 388
See application file for complete search history.

(56) References Cited

U.S. PATENT DOCUMENTS

| | | | |
|---|---|---|---|
| 4,063,097 A * | 12/1977 | Barrett et al. | 378/18 |
| 4,107,531 A * | 8/1978 | Garratt et al. | 378/16 |
| 4,157,472 A * | 6/1979 | Beck et al. | 378/4 |
| 4,455,609 A * | 6/1984 | Inamura et al. | 250/370.07 |
| 4,777,442 A | 10/1988 | Rosenthal | |
| 5,621,214 A * | 4/1997 | Sofield | 250/375 |
| 5,627,367 A | 5/1997 | Sofield | |
| 5,635,709 A | 6/1997 | Sliski et al. | |

(Continued)

OTHER PUBLICATIONS

Benedick Fraass; "Quality Assurance for Clinical Radiotherapy Treatment Planning," Med. Phys., 25 (10), Oct. 1998; pp. 1773-1829.

(Continued)

*Primary Examiner* — Carol S Tsai
(74) *Attorney, Agent, or Firm* — Allen, Dyer, Doppelt, Milbrath & Gilchrist, P.A.

(57) ABSTRACT

A three dimensional radiation measurement scanning system includes a circular drive operable with horizontal and vertical drives for moving a radiation detector through first, second and third orthogonal axes in a three dimensional scanning of the detector in a water tank. Motor are coupled to the drives and activated by a controller for providing the movement of the radiation detector which providing radiation field sensing signals for locations of the detector throughout the tank. A reference detector is fixed for comparing its radiation field measurements with those of the scanned radiation detector. An offset mount carries the radiation detector allowing it to be extended beyond the circular ring gear during horizontal movement of the radiation detector and thus position the radiation detector at wall surfaces of the water tank.

43 Claims, 7 Drawing Sheets

U.S. PATENT DOCUMENTS

| | | | |
|---|---|---|---|
| 5,640,436 | A | 6/1997 | Kawai et al. |
| 5,661,310 | A | 8/1997 | Jones |
| 5,873,826 | A * | 2/1999 | Gono et al. ............... 600/425 |
| 6,125,335 | A | 9/2000 | Simon et al. |
| 6,364,529 | B1 | 4/2002 | Dawson |
| 6,398,710 | B1 | 6/2002 | Ishikawa et al. |
| 6,594,336 | B2 | 7/2003 | Nishizawa et al. |
| 6,712,508 | B2 | 3/2004 | Nilsson et al. |
| 6,788,759 | B2 | 9/2004 | Op De Beek et al. |
| 6,853,702 | B2 | 2/2005 | Renner |
| 6,904,119 | B2 * | 6/2005 | Oikawa ..................... 378/15 |
| 6,904,162 | B2 | 6/2005 | Robar et al. |
| 6,974,254 | B2 | 12/2005 | Paliwal et al. |
| 7,098,463 | B2 | 8/2006 | Adamovics |
| 7,116,749 | B2 | 10/2006 | Besson |
| 7,127,028 | B2 * | 10/2006 | Sendai ..................... 378/21 |
| 7,142,634 | B2 | 11/2006 | Engler et al. |
| 7,193,220 | B1 | 3/2007 | Navarro |
| 7,233,688 | B2 | 6/2007 | Ritt et al. |
| 7,234,355 | B2 | 6/2007 | Dewangan et al. |
| 7,339,159 | B2 * | 3/2008 | Juh et al. ................. 250/252.1 |
| 7,352,840 | B1 | 4/2008 | Nagarkar et al. |
| 7,371,007 | B2 | 5/2008 | Nilsson |
| 7,386,089 | B2 * | 6/2008 | Endo et al. ................. 378/5 |
| 7,420,160 | B2 | 9/2008 | Delaperriere et al. |
| 7,471,765 | B2 | 12/2008 | Jaffray et al. |
| 7,605,365 | B2 | 10/2009 | Chen et al. |
| 7,668,292 | B1 | 2/2010 | Bose et al. |
| 7,734,010 | B2 | 6/2010 | Otto et al. |
| 7,766,903 | B2 | 8/2010 | Blumenkranz et al. |
| 7,773,723 | B2 | 8/2010 | Nord et al. |
| 7,778,383 | B2 | 8/2010 | Koehler et al. |
| 7,778,392 | B1 | 8/2010 | Berman et al. |
| 7,778,680 | B2 | 8/2010 | Goode, Jr. et al. |
| 7,782,998 | B2 * | 8/2010 | Langan et al. ............. 378/8 |
| 7,945,022 | B2 * | 5/2011 | Nelms et al. ............. 378/65 |
| 8,044,359 | B2 * | 10/2011 | Simon ..................... 250/370.07 |
| 8,093,549 | B2 * | 1/2012 | Navarro ................... 250/252.1 |
| 8,147,139 | B2 * | 4/2012 | Papaioannou ........... 378/195 |
| 2001/0042841 | A1 * | 11/2001 | Lyons et al. ............. 250/492.3 |
| 2002/0080912 | A1 | 6/2002 | Mackie et al. |
| 2003/0043960 | A1 | 3/2003 | Op De Beek et al. |
| 2003/0138077 | A1 | 7/2003 | Lee |
| 2004/0066880 | A1 * | 4/2004 | Oikawa ..................... 378/4 |
| 2004/0113094 | A1 * | 6/2004 | Lyons et al. ............. 250/435 |
| 2004/0120560 | A1 | 6/2004 | Robar et al. |
| 2004/0228435 | A1 | 11/2004 | Russell |
| 2004/0251419 | A1 | 12/2004 | Nelson et al. |
| 2005/0013406 | A1 | 1/2005 | Dyk et al. |
| 2005/0077459 | A1 | 4/2005 | Engler et al. |
| 2006/0002519 | A1 | 1/2006 | Jenkins et al. |
| 2006/0184124 | A1 | 8/2006 | Cowan et al. |
| 2006/0203964 | A1 | 9/2006 | Nyholm et al. |
| 2007/0195930 | A1 | 8/2007 | Kapatoes et al. |
| 2008/0049898 | A1 | 2/2008 | Romesberg, III et al. |
| 2009/0003512 | A1 | 1/2009 | Pouliot et al. |
| 2009/0252292 | A1 | 10/2009 | Simon et al. |

OTHER PUBLICATIONS

G.J. Kutcher; "Comprehensive AQ for Radiation Oncology Report"; AAPM Radiation Therapy Committee Task Group 40; Med. Phys., 21; Apr. 1994; pp. 581-618.

MapCheck and EPIDose; www.sunnuclear.com; manufactured by Sun Nuclear Corp. Melbourne, FL 2010.

MapCALC; www.sunnuclear.com manufactured by Sun Nuclear Corp., Melbourne, FL; 2009.

Joseph O. Deasy; "A Computational Environment for Radiotherapy Research," Med. Phys. 30, (5), May 2003; pp. 979-985.

Robert M. Eisberg; "Fundamentals of Modern Physics," Chapter 9-Perturbation Theory; John Wiley & Sons; 1967; pp. 268-272.

Cyberknife; Cyberknife System; "The Standard of Radiosurgery" by Accuray, Sunnyvale, CA; 2009; pp. 1-6.

"Hi-Art," www.tomotherapy.com; TomoTherapy, Madison, WI 2007; pp. 1-8.

"Rapid Arc"; Varian Medical Systems, Inc., Palo Alto, CA; www.varian.com; 2007; pp. 1-8.

"VMAT"; Elekta, Ltd., Crawley UK; Document No. 4513 3710770; Oct. 8, 2008.

D.W.O Rogers; "Montey Carlo Techniques in Radiotherapy,"; Physics in Canada, Medical Physics Special Issue, V. 58 #2, 2002; pp. 63-70.

T.R. McNutt, T.R. Mackie, P.J. Reckwerdt, B.R. Paliwal; "Modeling Dose Distributions from Portal Dose Images Using the Convolution/Superposition Method,"; Med. Phys. 23(8); Aug. 1996; pp. 1381-1392.

T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.

Mathilda Vanzijtveld, Maarten L.P. Dirkxa, Hans C.J. De Boera, and Ben J.M. Heijmen; "3D Dose Reconstruction for Clinical Evaluation of IMRT Pretreatment Verification with an EPID,"; Radiotherapy and Oncology, 82(2); Feb. 2007; pp. 201-207.

"Waterphantom Dosimetry"; Medical Physics, vol. 3, May/Jun. 1976; pp. 189.

Indra J. Das, Chee-Wai Cheng, Ronald J. Watts, Anders Ahnesjo, John Gibbons, X. Allen Li, Jessica Lowenstein, Raj K. Mitra, William E. Simon, Timothy C. Zhu; Accelerator Beam Data Commissioning Equipment and Procudures; Report of the TG-106 of the Therapy Physics Committee of the AAPM; Med. Phys. 35(9), Sep. 2008; pp. 4186-4215.

* cited by examiner

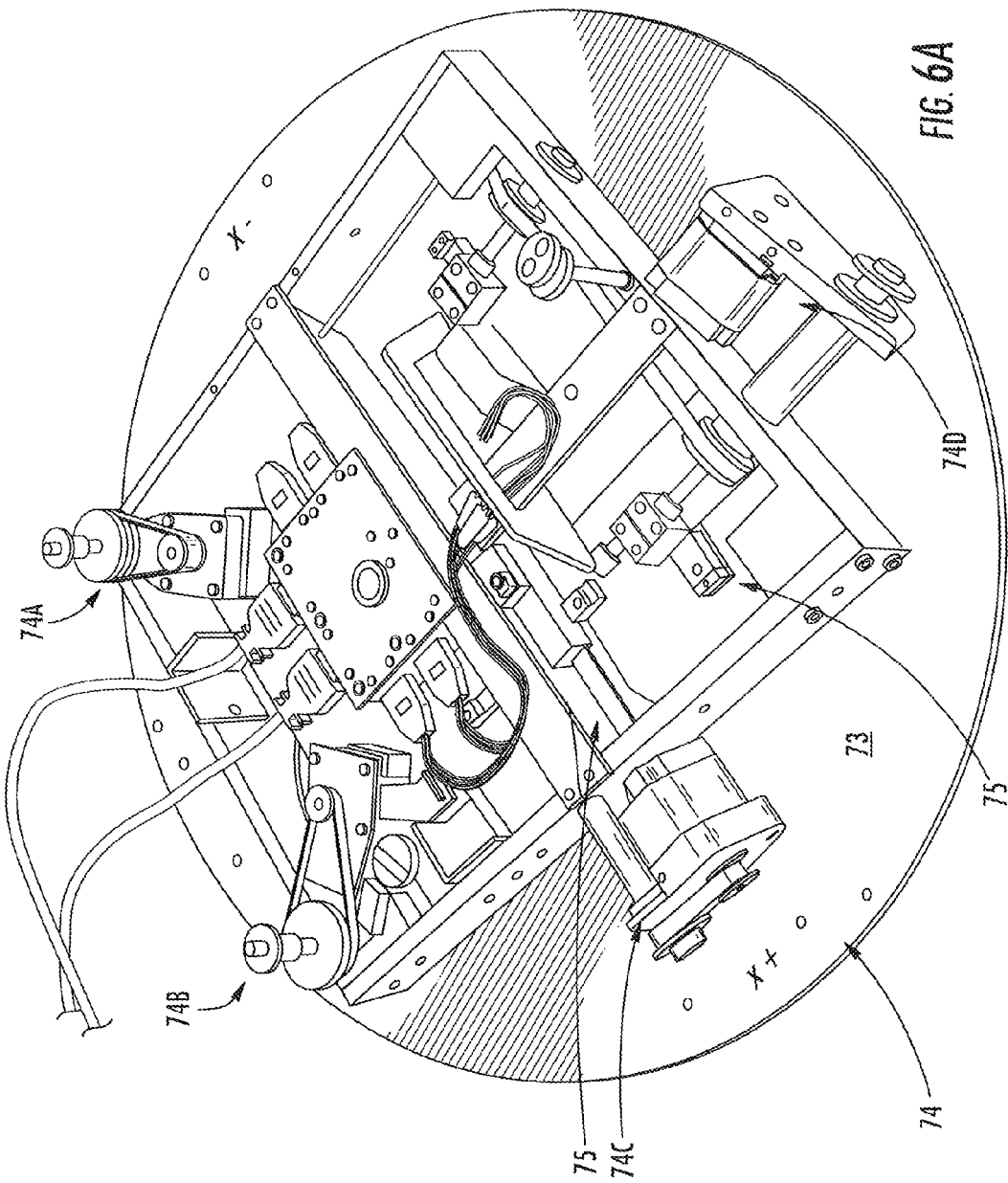

MULTIPLE AXES SCANNING SYSTEM AND METHOD FOR MEASURING RADIATION FROM A RADIATION SOURCE

CROSS REFERENCE TO RELATED APPLICATION

This application claims priority to Provisional Application Ser. No. 61/227,841 having filing date of Jul. 23, 2009 for "Three Dimensional Dosimetry Scanning System and Method Using Cylindrical Geometry," the disclosure of which is herein incorporated by reference in its entirety, and commonly owned.

FIELD OF INVENTION

The invention generally relates to radiation therapy equipment and radiation treatment, and in particular to systems and methods for measuring and localizing, spatially and/or temporally, the dose in a phantom for commissioning treatment planning systems in radiation therapy beam delivery.

BACKGROUND

Best standard practice for commissioning a linear accelerator for clinical use typically requires a three dimensional (3D) water tank dosimetry scanner (3DS). A 2008 AAPM report[1] "Accelerator Beam Data Commissioning Equipment and Procedures: Report of the TG-106 of the Therapy Physics Committee of the AAPM" (Indra Das—Chair) highlights the importance of the 3DS as well as a lack of easy to use systems currently available. The following excerpts provide guidance for the Performance Objectives of the 3DS.

From the above referenced TG-106 report (see Abstract): "For commissioning a linear accelerator for clinical use, medical physicists are faced with many challenges including the need for precision, a variety of testing methods, data validation, the lack of standards, and the time constraints. Since commissioning beam data is treated as a reference and ultimately used by treatment planning systems, it is vitally important that the collected data should be of the highest quality to avoid dosimetric and patient treatment errors that may subsequently lead to a poor radiation outcome. Beam commissioning data should be independent of the user and should be performed with appropriate knowledge and proper tools. To achieve this goal, Task Group 106 (TG-106) of the Therapy Physics Committee of the American Association of Physicists in Medicine (AAPM) was formed to review the practical aspects as well as the physics of linear accelerator commissioning."

Again, from the TG-106 report (see Introduction): Beam data commissioning should be independent of users and scanning systems if it is performed with appropriate knowledge and proper tools. Data variation among collectors should be as minimal as possible (<1%). To achieve this goal, the TG-106 report was prepared to aid users in all aspects of accelerator beam data commissioning by describing specific set-up and measurement techniques, reviewing different types of radiation phantoms and detectors, discussing possible sources of error, and recommending procedures for acquiring specific photon and electron beam parameters."

Also, the NEED, the PROBLEMS (issues), and the EFFORT of these measurements are defined with the following points that head a discussion on each. In particular, the time burden is emphasized in the third point:

"Need for commissioning data"
"Issues with beam commissioning measurements"
"Commissioning effort
" . . . The amount of commissioning data requirements depends on the of the user's clinical need, including the treatment planning system (TPS), monitor unit programs, in-house data tables, and the like. To account for equipment setup, change in machine parameters, machine faults, etc, the typical time for photon beam scanning is 1.5 weeks. An additional week is needed for point data collections, 1-2 week for electrons and a week for verification. Typically, 1-2 weeks are needed in analysis and report writing. The typical time allotted for the commissioning process is 4-6 weeks. . . . "

Therefore, there is a need for an accurate scan measurement of relative dose in a water phantom. Furthermore, there is a need for the 3DS water tank size to permit at least a 40×40 cm² field and a scanning depth of 40 cm[1-II.A "Phantom material"]. Furthermore, there is a need for the 3DS system to allow scanning in both cross- and in-plane (X and Y directions) and diagonal or star profiles[1-Table1 and II.A]. Quoting from the TG-106 report, (Section II. A Phantom Material) "Scanning in both dimensions provides convenience and avoids alignment problems associated with tank rotation."

Further consider guidance from the TG-106 report (Section II.B Dimension of phantom):

"The size of water tank should be large enough to allow scanning of beam profiles up to the largest field size required (e.g., for photon beams, 40×40 cm² with sufficient lateral buildup (5 cm) and over-scan distance. Some planning systems require larger lateral scans and diagonal profiles for the largest field size and at a depth of 40 cm for modeling. When considering the size of the scanning tank, the over scan and the beam divergence at 40 cm depth should be considered. A factor of 1.6 times the maximum field size should provide a safe limit. Simple calculation shows that at a maximum depth with consideration of over-scan and diagonal distance, a tank size of 75×75 cm² is recommended. If the scanning software does not have the ability to perform diagonal scans, the table pedestal should be rotated to acquire the desired data. . . . The size of the tank still needs to be much larger than 75×75 cm² to achieve the data with the same over-scan distance for diagonal profiles. In practical terms, however, very few commercial scanning systems are capable of scanning the full diagonal plus 5 cm over-scan at depths of >30 cm for 40×40 cm² field at 100 cm SSD. Some compromise could be made by taking only half scans. Consequently, half scans will have to be collected for these maximum field sizes, which require an offset of the tank relative to the central axis. Before setting up for half scans, it is important to verify that the open beam show minimal asymmetry (<0.5%). . . . "

These guidelines are written by users of 3DS systems, keeping in mind the general concepts of 3DS systems that are commercially available. The guidelines, although published in 2008, are not new concepts since the 40 cm field sizes and TPS requirements have been around for decades. Thus, there has been a disconnect between a desirable scanning system to meet the performance needs of the application and what has actually been commercially available.

Water tank scanning dosimetry systems have been commercially available since the 1970s and probably earlier. Their designs incorporate orthogonal linear axes, the earlier units being a two axes system, one for depth and the other for horizontal "beam intensity profile" scans. To change a scan axis from beam in-plane to beam cross-plane, the operator would typically rotate the tank. Later as design sophistication came about, another horizontal axis was added (orthogonal to the other horizontal axis) making a three dimensional system, with the ability to scan to any location within the axes' scanning range. By the nature of the scan axes, these 2D and 3D systems used a "rectangular or orthogonal axis" geometry and were mounted in rectangular tanks that hold water. By way of example, Artronix Incorporated provided System 3302 three axis system in rectangular shape. It is of interest to note that a journal advertisement appeared in Medical Physics, 1976. This was a natural evolution to the radiation machines such as Co-60 units and linear accelerators (LINAC). The collimators ride on two axes, the in-plane and cross-plane, which produce square or rectangular radiation fields. Computer controls on linear axis drive systems were commonly available, making linear axes a natural selection. Scanning the beam to measure the radiation intensity distribution requires means to periodically measure the radiation "field" sensor, radiation detector, output at temporal or spatial increment positions as the sensor is moved through the water, and means to record these measurements for later analysis. The sensor will move perpendicular to the beam axis to measure the profile of beam intensity as a function of distance from the central axis of the beam. Such a movement will normally be parallel to the water surface when the beam is directed into the open top of the water tank, but could also be perpendicular to the water surface if the beam is directed through the sidewall of the water tank.

A measurement with the detector movement parallel to the beam axis would be a depth dose curve, i.e., the change in beam intensity as it transmits through the water and suffers beam divergence, otherwise known as "percent depth dose" (PDD). The measurement of the sensor is normally done in conjunction with a reference sensor that is stationary in the beam and positioned such that it does not interfere with the detector/sensor. Both sensors, radiation and reference, are measured simultaneously so that any change in beam intensity from the LINAC itself is normalized out by taking a ratio of the measurements.

Nearly all LINACs have a maximum field size of 40×40 cm; Varian[2] LINACs have a primary collimator beam limiting geometry with rounded corners that result in a 50 cm maximum diagonal in a 40×40 cm field. Other manufacturers may have similar geometries. As discussed in the TG-106 report, this defines the tank geometry requirements if the scanner is to measure the beam and 5 cm outside of beam at both sides at a maximum depth of 40 cm. There is a need for scanning systems to perform these measurements. To overcome this in typical systems, the scanning system (and the tank) is shifted off center in order to measure the diagonal and 5 cm out of beam. For example, with the source to surface distance (SSD—water surface to LINAC target) at 90 cm, the 40×40 cm field at 40 cm depth extends to 47×47 cm. A 5 cm out of beam measurement extension requires an additional 10 cm, or a scan dimension of 57×57 cm. This exceeds the capabilities of most if not all commercially available scanners. The PTW[3] MP3-M has approximate inner tank dimensions of 59.6 cm×59.4 cm and 50.6 cm depth. However, the scan dimensions are typically limited by the mechanical overhead of pillow blocks and stops that restrict the scan dimensions to approximately 54 cm×50 cm and 40.8 cm depth. The IBA Scanditronix Wellhofer[4] RFA-300 has 49.5 cm×49.5 cm×49.5 cm scanning dimensions on the 3 linear orthogonal axes, again smaller than the desired 57×57 cm scan range when scanning all the geometries of a 40×40 cm field.

When the profile measurement nears the beam edge, there is a steep drop off in beam intensity as the sensor moves out of the beam. This beam edge, or "penumbra" region includes important information for the planning system and is used in commissioning the dose model of the treatment planning system (TPS) for the LINAC being commissioned. The shape of the penumbra region can be affected by the sensor geometry and if the sensor does not have scan direction symmetry, the relative penumbra shape may also be dependent upon the scan direction if the sensor is not re-oriented before scanning, i.e. does not have the same orientation for both scan directions. (See TG-106 §IV.A.4 Beam Profiles). Using a conventional three axis scanner, in order to keep the same detector orientation in profile scans that are orthogonal (ex: X and Y, cross-plane and in-plane, transverse and radial), the detector mount would be rotated 90 degrees. Some of the scanners have this provision with a detector mount that can be rotated, but this requires a trip into the LINAC room and runs the risk of disturbing the setup. A two dimensional scanner (one vertical, one horizontal) would require rotation of the scanner itself to make the orthogonal scan. It would keep the detector properly oriented but with the burden of a trip into the room and disturbance of the scanner setup.

The sensors are typically chosen by the medical physicists from an array of available sensors that may or may not be best suited for the measurement conditions, such as electrometer noise and signal (gain), field size, beam intensity from the LINAC, beam edge penumbra width, and beam type (electrons or X-rays). These issues are discussed in the TG-106 report and generally contribute to the problem of the beam scan measurement results not being unique to the beam but dependent on the operator and equipment.

Sensor size plays an important role on penumbra measurement, with larger dimensions in the scan direction contributing a larger error in the penumbra measurement. There are methods to correct for these "convolution" errors resulting from volume averaging of the sensor, as reported by JF. Dempsey[5]. However, this "de-convolution" correction method is complex and typically not available in the scanning systems. If corrected, as demonstrated by G Yan[6], it would be done so after scanning, outside of the scanner system analysis software.

Therefore, there is a need for scan analysis, concurrent with the scanning system profile measurement, which provides a de-convolution of the chamber scan data that results in an accurate determination of the true beam profile shape and which provides the user the confidence to continue with the other beams before closing the LINAC measurements. A consistent data set is important for commissioning the TPS system, as stated in both TG-106[1] and TG-53[7] reports. Consistency is best achieved in a contiguous measurements work flow that results when there is no need to repeat measurement in repeated setups.

The measurement session of the LINAC beam scanning can take many days as discussed in the TG-106 report. During these long scanning times, there are no assurances from the scanner system to indicate that the scanner system or the LINAC has not changed during scans in a way that would affect the measurement data. It is incumbent upon the operator to perform periodic quality assurance (QA) tests that would reveal such changes in the scanner system. This was the basic scope for TG-106 report, to provide insight to the operator who only occasionally performs the scanner measurements. There is a need in the scanner system to provide system QA tests which would reveal changes in the scanner operation that could cause or influence a change in scan measurements over the duration of the scanning sessions, both intersession i.e., between sessions separated by setup change, beam condition change (6 MV vs. 15 MV), day change, etc, and intrasession, i.e., within a session itself.

The measurement session of the LINAC beam scanning will consist of many setups and data structuring as discussed in the TG-106 report. During these many setup changes and tedious measurements, the operator may incorrectly identify data with particular setups. For example, unintentionally interchanging the labels on scan axes; or not changing the LINAC energy when the scan queue changed; or the collimator of the LINAC is rotated 90 degrees on a symmetric field without the user being aware. These types of setup errors are difficult to see after the sessions have ended and the data saved. The operator can open the data and examine the profiles, but there is generally not enough characteristic uniqueness to the data to easily identity an error, particularly if the operator is not very experienced, or even with experienced operators, when the error is a collimator rotation of 90 degrees. There is a need in the scanner system to provide setup QA tests that would reveal unique characteristics associated with the setup identifiers in the data that is to be saved.

SUMMARY

Based on the forgoing described needs, embodiments of the invention may comprise a multiple axes scanning system for measuring radiation from a radiation source. Such a system may comprise a processor having means for analysis and data storage and a controller operable with the processor. A ring drive may be operable with the controller for providing a rotational movement about a first axis responsive to a command therefrom. A horizontal drive may be operable with the controller for providing horizontal movement along a second axis, wherein the horizontal drive may be operable with the ring drive for receiving a rotational movement therefrom about the first axis. A vertical drive may be operable with the controller for providing a vertical movement of the horizontal drive along a third axis responsive to a command therefrom. A radiation detector may then be carried by the horizontal drive for receiving the horizontal movement therefrom. (For fixed radius circular scanning, a radiation detector may also be carried by the Ring drive.) The radiation detector provides sensing signals to the processor for locations of the radiation detector orientated through circular, horizontal, and/or vertical movement along the axes as commanded by the controller.

Yet further, the present invention may provide a system and method, wherein one embodiment may be provided as herein referred to as 3DS™ and 3D Scanner™ that may comprise a scanning system having three axes, one forming a circular ring drive, one forming a linear drive essentially along the diameter of the ring drive, and one forming another linear drive essentially vertical to the diameter of the ring drive, with electronics capability to independently control all three drives such that a radiation sensor mounted to the horizontal drive can be located, using any or all of the axes, at any desired location for beam measurement and connected to electronics capability to measure the sensor's response to radiation (such as an electrometer, by way of example) and record the sensors response and location on the three axes. This described cylindrical three axis scanning system will scan the LINAC beam profile axis (X, Y, diagonals, and star through beam center) using the same drive and same detector orientation without the need to disturb the scanner system. This is accomplished with remote electronics control capability. The use of the same drive for all profiles provides the benefits including, by way of example, each profile measurable on the same axis drive locator which cancels differences in linear transfer functions that may exist between different axis drives, for example in a 3 axis linear system where the X and Y are two distinct drives even if they are identical in design. Each profile measurement may have a minimum and identical mass movement in a water scan, providing minimum water disturbance that may influence the beam transmission through water. (See TG-106) In a 3 axis linear system, one axis (e.g. X) carries the sensor which provides minimum mass movement, but the other axis (eg. Y) must move the entire axis (e.g. X) that carries the sensor when the other axis (eg. Y) is required for the orthogonal profile, i.e., Y axis profile is orthogonal to X axis profile. Each profile may be measured with the same sensor orientation with respect to the scan direction. Normally, the sensor will be oriented with its smallest dimension moving along the scan axis, providing the least volume averaging in the penumbra. In a conventional 3 axis linear system, one axis carries the sensor so that the dimension 'X' moves along the axis, but when the orthogonal axis profile is selected for measurement, dimension 'Y' moves along the scanning axis, carrying the X scanning axis and the sensor oriented for X axis scanning.

The cylindrical three axis scanning system may be mounted in a circular cylindrical tank. A circular cylindrical tank is not a requirement to benefit from the cylindrical three axis scanning system. The tank circular cylinder may be a more rigid structure to hold water than a rectangular (or square) tank, which may have deformation on the sidewalls due to water pressure if the tank walls are not sufficiently thick. A circular cylinder also is a more efficient use of area footprint when considering scan dimensions. Other tank geometries may also be used with the cylindrical three axis scanning system with suitable mechanical mounting.

The present invention also provides an improvement in a method of mounting the radiation detector with an offset from the center of the scan axis which enables full access to the tank edge, thereby extending the scanning range and eliminating the need to shift the system (scanner and/or tank) when scanning large field sizes. In particular to the embodiment herein described by way of example with a 66 cm inner diameter tank, it becomes possible to scan the largest field size (40 cm×40 cm at isocenter, to the axes and diagonals, as addressed above) in two segments per profile with their scan centers offset on either side from the ring drive center. The segments can be scanned with both directions without user intervention by a ring rotation, or the user can reposition the offset mount and rescan in the same direction. The present invention provides further improvement with reference detector and one or more radiation detectors wherein the multiple detectors, connected to electronic means, are mounted at various points on the scan axis, offset on both sides of the axis center as well as the possibility of one detector on the axis center, enabling the full field scan in one scan of the detectors. The overlapping scan regions provide means by which analysis means may normalize and concatenate partial scans of all detectors into one field scan.

A water surface sensor may be provided including an ultrasonic surface sensor or capacitive surface sensor having a sharp conductive point connected to electronic means of contact detection, that when mounted on the linear horizontal drive, measures the water surface at three or more non-collinear position (a surface) by adjusting the vertical drive until the surface is located. The software may then analyze the level error of the three dimensional cylindrical scanning system with respect to the water surface and either instruct the operator to make level adjustments with leveling means that may include scaled adjustment controls, or adjust motorized leveling screws, or compensate for the level error with instructions to the three dimensional cylindrical scanning system control in such a way that keeps the radiation field sensor level (parallel) to the water surface.

The present invention provides an improvement in a method of profile analysis that determines the beam penumbra from the scanned penumbra by de-convolution of the scanned detector response, where the de-convolution method uses the chamber spread function that is determined in these analysis means from data measured with the scanning detector that exhibits penumbra spreading and another detector that does not exhibit significant penumbra spreading, both scanned with these scanning means. The present invention provides an improvement in the method of confidence in beam scanning by providing analysis means that may calculate ratios of normalized orthogonal scanned beam profiles, resulting in a values (plot) of the radial homogeneity of the radiation field, and provides a comparison of the penumbra shape that is characteristic to beam shapers such as jaw positions (upper and lower), MLC leaf ends and leaf sides, as two examples. Ratios of percent depth dose curves (PDD) may be calculated, normalized at same depth, measured at different beam energies, resulting in values that trend up or down, depending upon the actual beam energy, thereby providing comparison means with expected trend. Given the same field size, higher beam energy PDD divided by lower beam energy will produce values than trend upward, i.e., increase in value with increase in depth. Ratios of normalized profiles measured with the same beam geometry but measured at different times in the queuing process may be calculated, resulting in a values (plot) that that should not change if no physical setup changes occurred, no physical operating conditions of the scanning system occurred, no changes in the LINAC radiation delivery occurred. Analysis of these ratio values will reveal slight shifts in the scanner reference position by causing differences in the penumbra regions, changes in the beam limiters, changes in the LINAC beam shape, to name a few. Ratios of normalized scans (profiles and PDD curves) may be calculated that have corresponding LINAC setup conditions that were measured in a reference set of LINAC measurements that are known to be good, i.e., golden or benchmark data. Such a data set was determined by Sun Nuclear Corp under an SBIR contract "Establishment of Benchmark Data Sets for Radiotherapy Quality Assurance" with the National Institute of Health's National Cancer Institute Contract No. HHSN261200522014C, ADB Contract No. N43-CM-52214.

BRIEF DESCRIPTION OF DRAWINGS

Embodiments of the invention are described by way of example with reference to the accompanying drawings and illustrations in which:

FIG. 6A is an underside open view of one adjustment means providing a motorized level and shift platform;

DESCRIPTION OF EMBODIMENTS

The present invention will now be described more fully hereinafter with reference to the accompanying drawings, in which embodiments of the invention are shown. This invention may, however, be embodied in many different forms and should not be construed as limited to the embodiments set forth herein. Rather, the embodiments herein presented are provided so that this disclosure will be thorough and complete, and will fully convey the scope of the invention to those skilled in the art.

Figure 1:
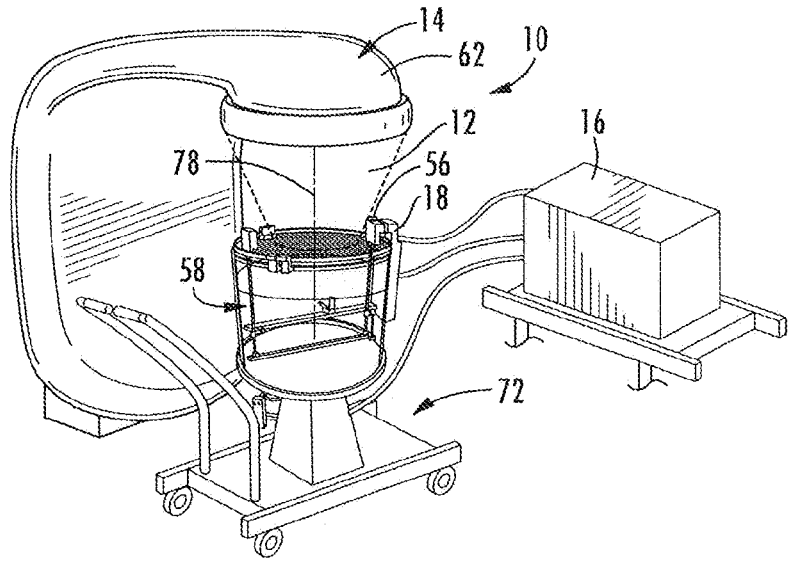
FIG. 1 is a partial perspective view of one embodiment of the invention operable with a LINAC for radiation dose measurements.

By way of example, and with reference initially to FIG. 1, one embodiment of the invention, herein described by way of example, is a multiple axes scanning system 10 for measuring radiation 12 emitted from a radiation source 14. The system 10 comprises a processor 16 having analysis and data storage capabilities and a controller 18 operable with the processor.

Figure 2:
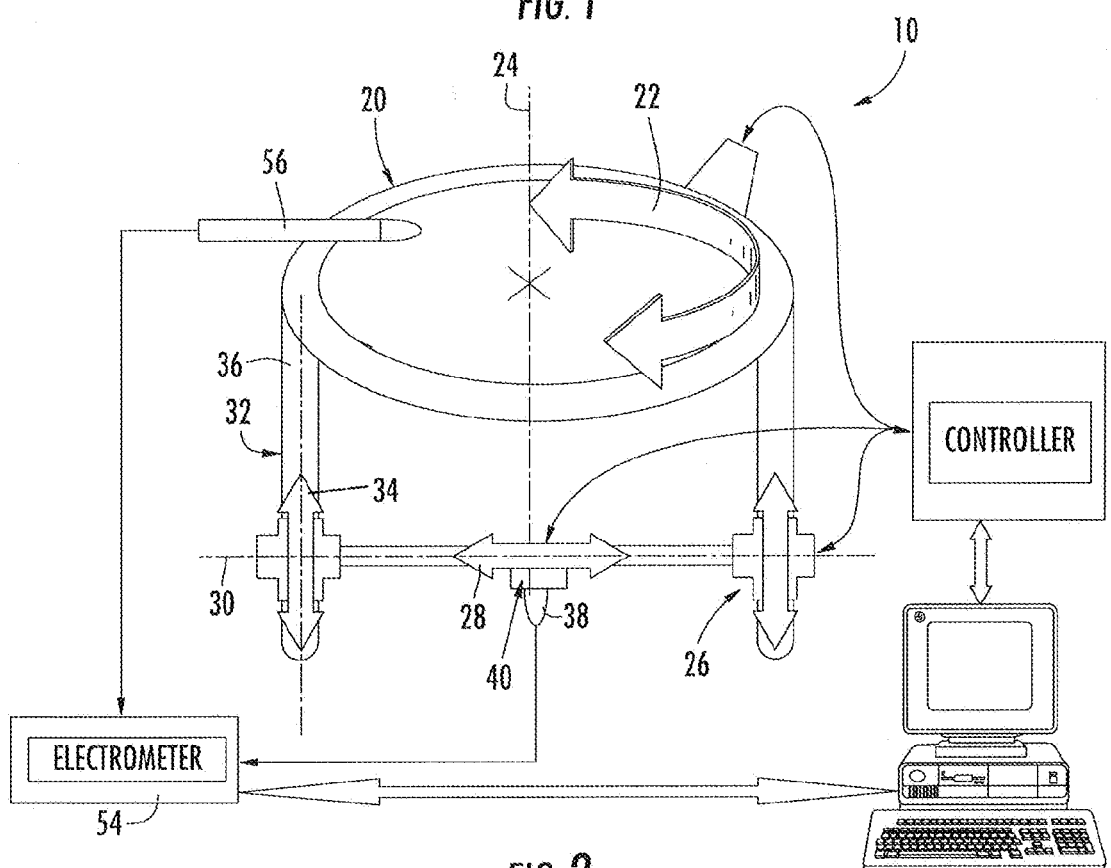
FIG. 2 is a diagrammatical illustration of a cylindrical scanning system in keeping with the teachings of the present invention.

With reference to FIG. 2, a ring drive 20 is operable with the controller 18 for providing a rotational movement 22 about a first axis 24 responsive to commands from the controller. A horizontal drive 26 is operable with the controller 18 for providing horizontal movement 28 along a second axis 30. For the embodiment herein described by way of example, the horizontal drive 26 is operable with the ring drive 20 for receiving the rotational movement 22. A vertical drive 32 is operable with the controller 18 for providing vertical movement 34 of the horizontal drive 26 along a third axis 36 responsive to the commands from the controller 18. A radiation detector 38 carried by a mount 40 affixed to the horizontal drive 26 for locating it along the drive 26 by the horizontal movement 28. The radiation detector 38 provides sensing signals to the processor 16 for selected locations of the radiation detector when orientated through the circular (rotational), horizontal, and vertical movements 22, 28, 34 along the first, second and third axes 24, 30, 36, respectively, as a result of the commands from the controller 18.

Figure 3:
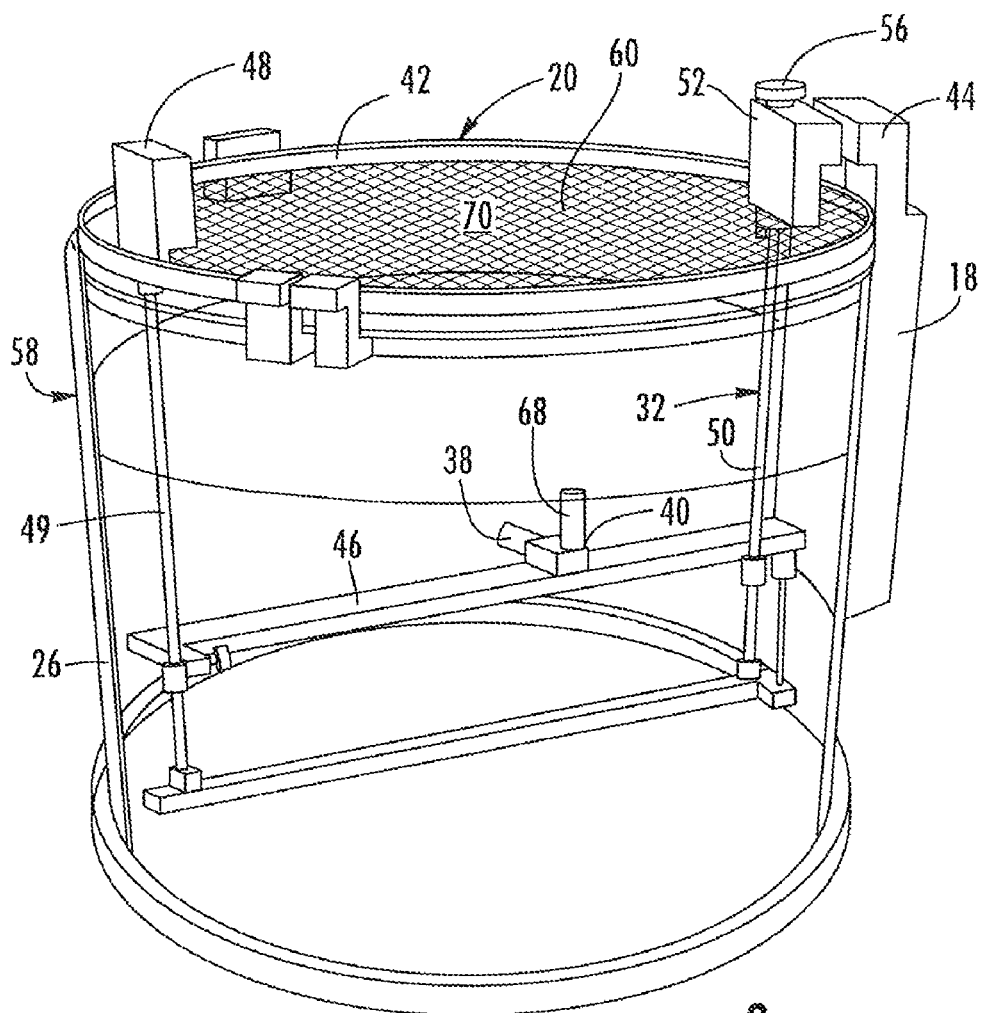
FIG. 3 is a perspective view of one embodiment of the invention illustrated in FIG. 1.

As illustrated with reference to FIG. 3 for the embodiment herein described by way of example, the ring drive 20 comprises a circular gear 42, wherein the controller 18 operates with a first motor 44 operable with the circular gear for providing the rotational movement 22. The horizontal drive 26 comprises a belt and pulley assembly 46 driven by a second motor 48 and shaft 49 operable for moving the radiation detector 38 horizontally. The vertical drive 32 comprises a screw gear 50 driven by a third motor 52 mounted to the ring drive 20. While individual motors are herein described by way of example, alternate gearing and linkages will come to the mind of those skilled in the art now having the benefit of the teachings of the present invention.

With reference again to FIG. 2 the system 10, herein described by way of example, comprises an electrometer 54 operable between the processor 16 and the radiation detector 38. In addition, a reference detector 56 is located at a fixed location for comparing the sensing signals from the radiation detector 38 to the reference detector. As illustrated with reference again to FIGS. 1 and 3, a cylindrical water tank 58 carrying water 60 is dimensioned for movement of the radiation detector 38 is provided and supports the drives 20, 26, 32 described above. The controller 18 is capable of communicating movement commands and receiving encoder information from the motors and bi-directional communication of movement command and encoder position data to the programmable processor 16, synchronized to the bi-directional communication of the detectors 38 and 56 from the electrometer 54.

The embodiment herein described is by way of example only for one application for the cylindrical scanning system 10. However, other geometrically shaped vessels may be employed without compromising the benefits of the cylindrical scanning system. During scans, the vessel may contain water, or air scans may also be performed with an empty vessel, depending upon the requirements of the operator and the TPS. Furthermore, the system 10 may be implemented without a vessel and assembled in a self supporting frame that rests on the treatment couch or mounted to the head of the radiation source such as a LINAC™ for testing radiation beam characteristics as the gantry 62 is moved, as referenced in FIG. 1.

Figure 4:
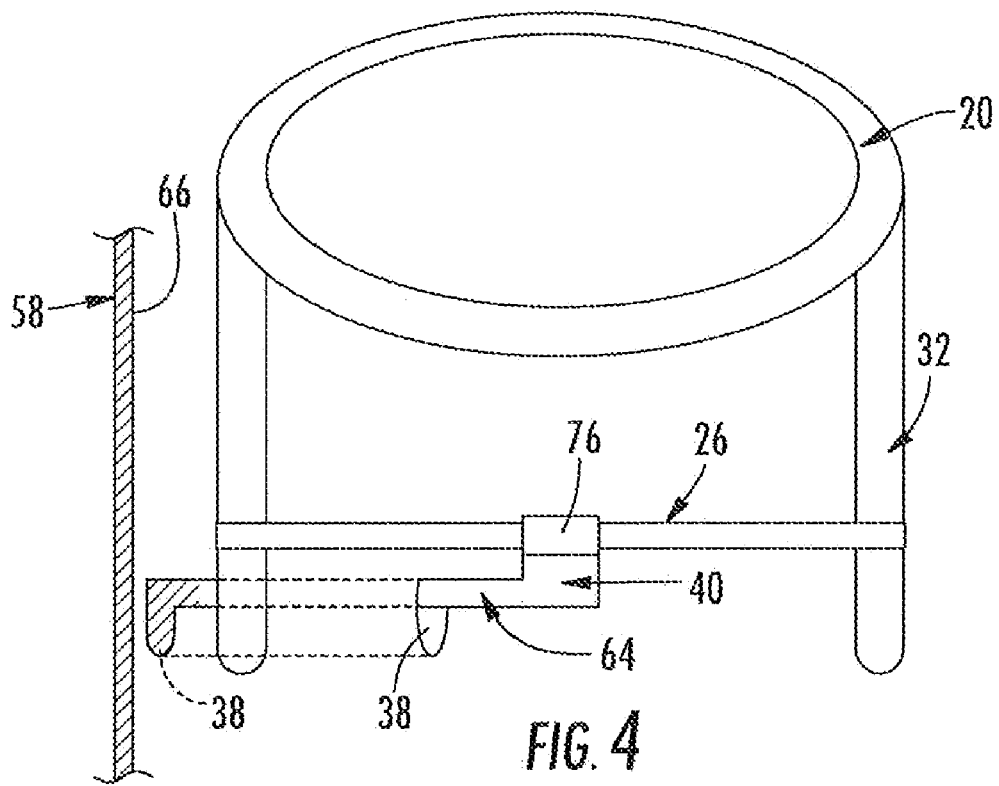
FIGS. 4 and 5 are partial diagrammatical illustrations of detector offset mounts used with single and multiple radiation detectors.

With reference now to FIG. 4, the mount 40 may comprise an offset mount 64 operable with the horizontal drive 26, wherein the offset carries the radiation detector 38. The offset mount 64 is dimensioned for extending the radiation detector 38 up to or closely proximate an inside wall surface 66 of the vessel 58 during a scanning movement of the radiation detector. The offset mount 64 may comprise multiple detectors 38a, 38b, 38c as desired and illustrated with reference to FIG. 5, by way of example.

With reference again to FIG. 3, a surface sensor 68 is included for determining a location of a surface 70 of the water. The surface sensor 68 in one embodiment is carried by the horizontal drive for allowing measurements to be taken at multiple non-collinear positions by movement of the vertical drive 32 for locating the surface of the water 70. The surface sensor 68 may include an ultrasonic sensor, a capacitive sensor, or alternatives as desired.

Figure 6:
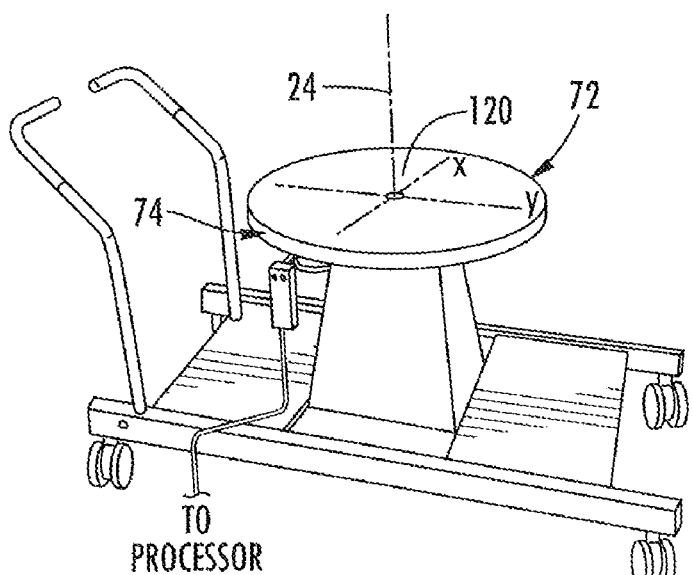
FIG. 6 is a perspective view of one embodiment of a table for carrying a water tank illustrated in FIG. 1.

With reference again to FIG. 1 and now to FIG. 6, a table 72 is employed for supporting the vessel 58. Adjustment means 74 is operable with the table 72 for providing a leveling of the table and an axis adjustment 76 for operation with the radiation detector 38 thus providing an alignment of the first axis 24 of the ring drive 20 to a beam axis 78 from the radiation source 14.

With continued reference to FIGS. 1 and 6, and with reference now to FIG. 6A, one embodiment of the adjustment means 74 includes two leveling motors 74A (operable with a leveling foot) and 74B (operable with a leveling foot) provide independent vertical movement of a platform 73 carried by the table 72. In addition, two linear shift motors 74C (providing a linear shifting for +/−Y axis movement) and 74D (providing a linear shifting for +/−X axis movement) are each operable with rails 75 that provide independent horizontal movement of the platform 73 in an orthogonal X and Y direction. The water tank, vessel 58 is positioned on a top side of the platform 73A. During operation of the system 10, the processor 16, using the water surface sensor 68 locates the first axis 24 and any tilt error with the water surface and then commands the 74A and 74B motors to adjust the platform 73 to be level with the water surface 70. The processor 16, using the horizontal drive 26 for scanning the radiation detector 38, locates the beam axis 78 (a LINAC central axis (CAX) by way of example) on the X axis, then rotates the circular gear 42 by 90 degrees. The same operation is performed on the Y axis (CAY). The processor 16 commands the X and Y motors 74C, 74D to adjust the platform 73 to the X CAX and Y CAX.

Figure 5:
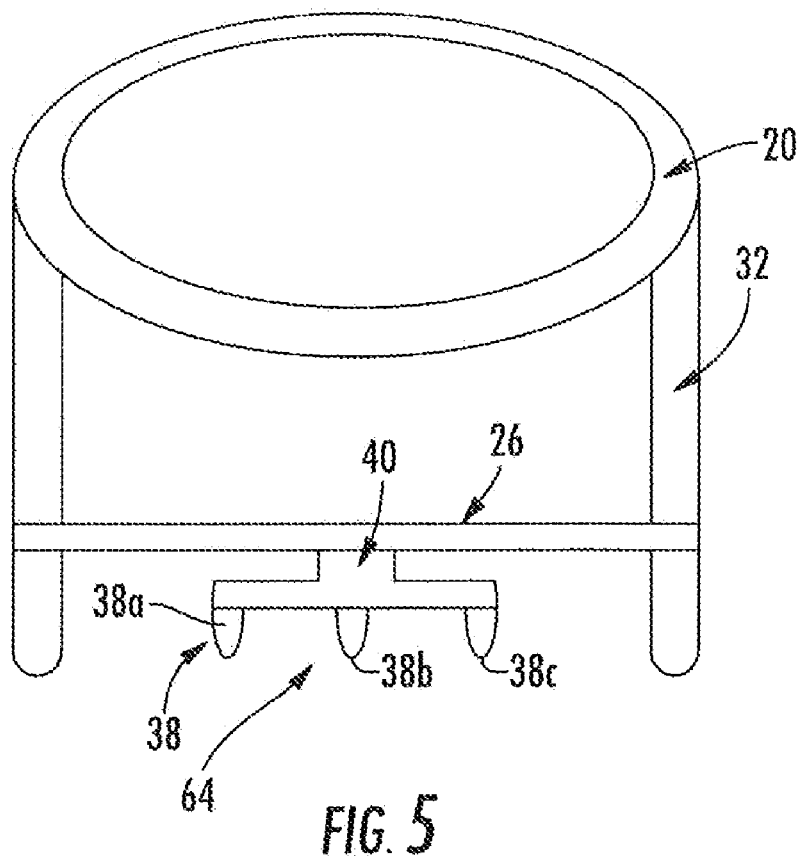

As will be appreciated by those skilled in the art, now having the benefit of the teachings of the present invention, an additional gear 76 may be used to rotate the extended detector 38 as illustrated with reference again to FIG. 4, by way of example. Alternatively, multiple offsets may be employed, as illustrated in FIG. 5 with the mount 40 showing a center mount for a center field detector 38b, a right offset mount for a right field detector 38c, and a left offset mount for a left field detector 38a. Other mount offsets with various numbers of detectors will become obvious for those skilled in the art. Note that the center mounting may be omitted in some configurations.

With regard to functionality of the system 10 and to further aid the reader, the following discussion is provided as reported by W Simon[8] for "Scan De-Convolution and Chamber Spread Function."

Experimental dosimeters always measure weighted integral dose over a limited geometric region. This effect can be characterized by a spread function, K, that represents physical phenomena of the spatial extension and spatial sensitivity of the dosimeter. The influence of a detector spread function can be eliminated by deconvolving the spread function from the measured dose distribution $D_m$ employing the Fourier deconvolution theorem:

$$\tilde{D} = \frac{\tilde{D}_m}{\tilde{\kappa}}$$

where $\tilde{D}$, $\tilde{D}_m$, and $\tilde{\kappa}$
are the Fourier transforms of the actual dose distribution D, the measured dose distribution $D_m$, and the spread function of the dosimeter κ. A numerical method for performing the deconvolution can be developed using the following model for the shape of MV photon beam penumbra: (JF Dempsey, "A Fourier analysis of IMRT dose grid resolution", Med Phys, 32, 380-388, 2005)

$$P(x) = \frac{1}{2} \cdot \sum_{i=1}^{N} a_i \cdot \left[ \text{erf}\left(\frac{x+b_i}{\sigma_i}\right) - \text{erf}\left(\frac{x-b_i}{\sigma_i}\right) \right]$$

where P is the dose profile, $a_i$ is an amplitude, $b_i$ is an effective field size, $\sigma_i$ the standard deviation of the erf function, given by:

$$\text{erf}(x) = \frac{2}{\sqrt{\pi}} \cdot \int_0^x e^{-t^2} \cdot dt$$

Figure 7:
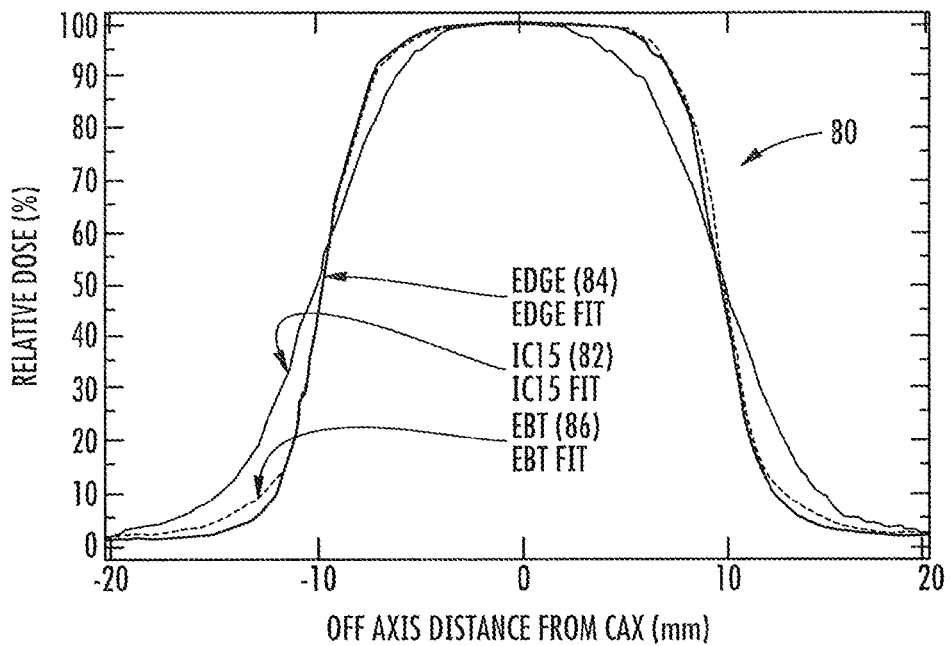
FIG. 7 illustrates a 2 cm radiation field profile, produced by in-plane jaws of a Varian linear accelerator that is measured by various detectors, one of which exhibits the need for de-convolution.

Radiation dose profiles 80 are illustrated with reference to FIG. 7, wherein a 2 cm field produced by in-plane jaws of a Varian linear accelerator at 6 MV and modeled (fit) with P(x) for N=2 is illustrated by way of example.

The Fourier transform of P is known to be:

$$\vec{P}(\omega) = \sum_{i=1}^{N} 2 \cdot a_i \cdot v_i \cdot e^{-\pi^2 \cdot \sigma^2 \cdot \omega^2} \cdot \mathrm{sinc}(2\omega v_i)$$

Thus, we can find the Fourier transform of the spread function, κ, by a deconvolution of the measured and true profile. The raw scan data in FIG. 7 illustrate the significance of the measurement uncertainty with a chamber 82, and also the measurement redundancy between a diode 84 and film 86. Notice that the Edge 84 and EBT 86 trace out an identical profile, thus validating each other. The IC15 (Wellhöfer model CC13 ion chamber 82 dimensions 6 mm ID×5.8 mm length, 0.13 cm$^3$ volume) has a significant amount of volume averaging in the penumbra illustrated by the shallower slopes. The penumbrae, measured from 20 to 80 percent by Edge and EBT, are 2.2 to 2.3 mm on both sides that clearly exceeds a Nyquist spatial frequency limit of the IC15. Each measured profile has an associated modeled profile that utilizes the error function erf(x) as discussed above. The deconvolution will eliminate the effect of the detector-spread function on the measured data set. In order to apply the deconvolution the field edge must be scanned until the dose reaches the collimator transmission level plus the distance where the spread function has effectively fallen to zero. The film dose calibration curve was measured several weeks apart from this profile measurement. This resulted in the deviation from the diode data outside the penumbra in the low dose region. The EBT film may require frequent calibration for application in low dose regions.

Figure 8:
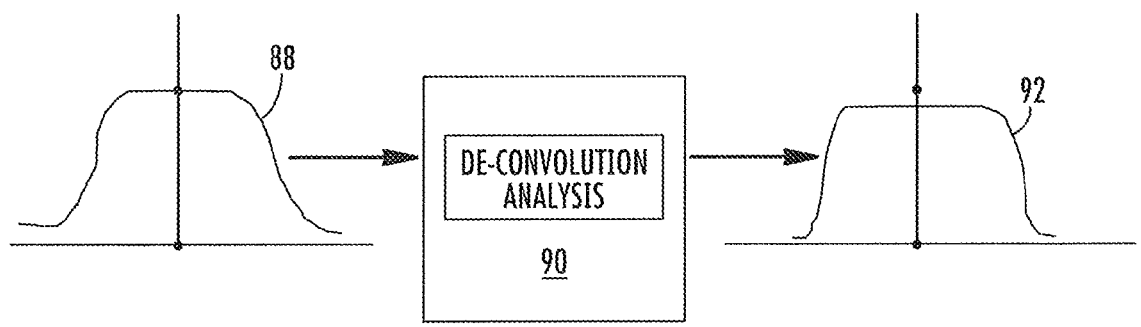
FIGS. 8 and 9 are diagrammatical illustrations of de-convolution analyses.
Figure 9:
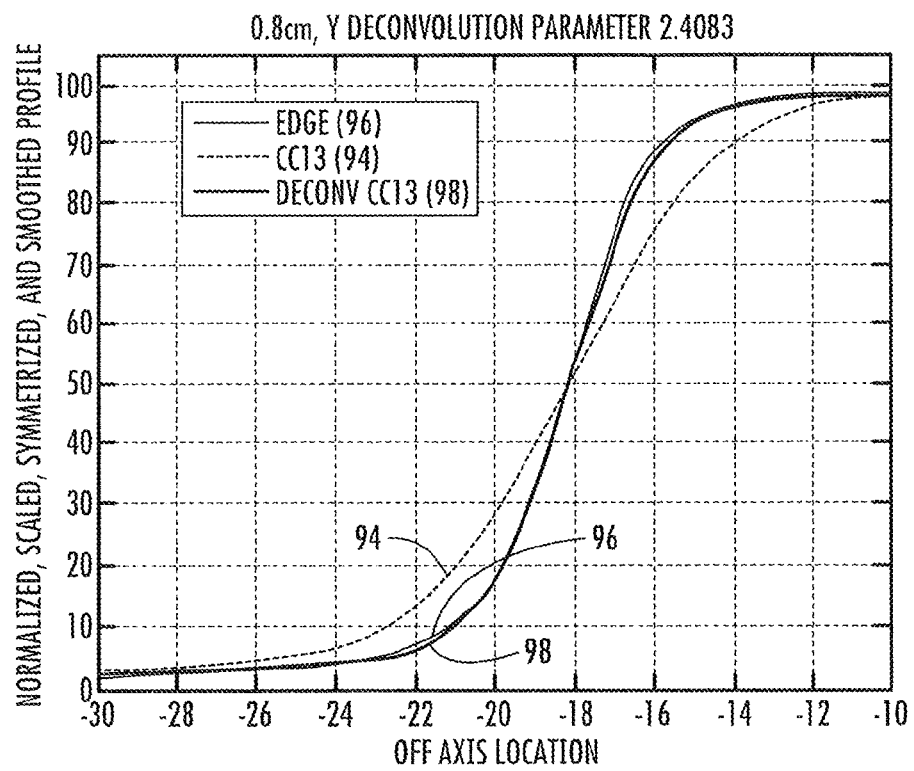

By way of further example, and with reference to FIG. 8, one overview of the de-convolution is illustrated with a scanned profile 88 being processed with the de-convolution analysis 90 that results in a modified profile shape 92 that represents an improvement of the true beam intensity of the LINAC. An illustration of the this process is represented with reference to FIG. 9 by which one scanned profile 94 from one field detector, an IBA[4] ion chamber sensor named "CC13", is spread out compared to a scanned profile B96 96 from the radiation detector 38, earlier described with reference to FIG. 2, a Sun Nuclear[9] small diode sensor named "EDGE". The EDGE detector profile was analyzed for the true beam shape from which was derived the de-convolution parameter (2.4083) which, by de-convolution analysis, produced the de-convolved profile 98. The de-convolution parameter is used in the analysis of all the CC13 scans as they are produced, resulting in nearly "real-time" visualization of the true profile immediately after scan. This allows immediate comparison to other known profiles before saving the scan data for clinical use.

Figure 10:
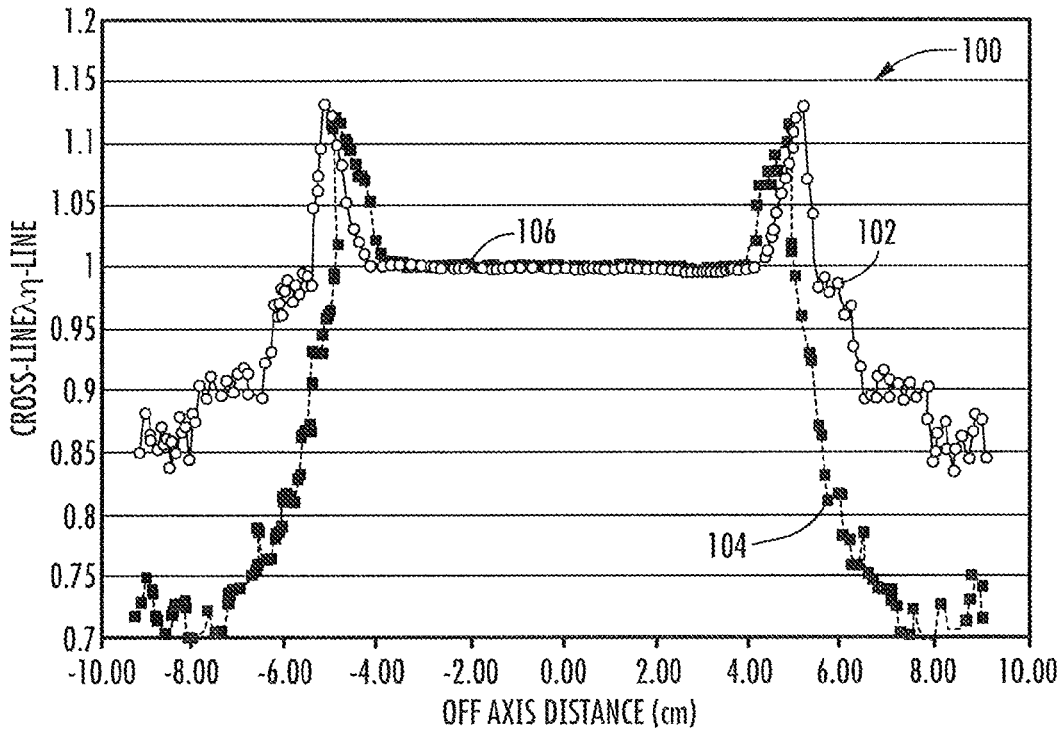
FIG. 10 illustrate radiation profiles for a Varian radiation field uniformity at two depths (1.5 cm and 10 cm) within a water tank (Varian Radial Homogeniety of Profile scan field, 90 SSD, Raw Symmetrized Scan Data)

By way of example, and with reference to a data plot of FIG. 10, one overview of results from a QA method of the present invention is illustrated as ratios X/Y of the profiles 100 scanned on the X and Y axes of the Varian[2] LINAC at two different scan depths of the radiation detector 38 below the surface 70; 10 cm 102 and 1.5 cm 104 below the water surface. In the flat portion 106, the profile ratio varies less than 1% between the two axes, in 86% of the field size. Then as the scan enters the penumbra region as earlier described, the ratio increases to almost 12% and then drops, which indicate the X axis (in-plane) has a sharper penumbra, wherein the scan value stays higher as the scanned radiation detector 38 enters the beam edge penumbra, and lower jaw transmission. The location of the Varian X axis collimator jaw is lower (closer to the scanning detector 38 and therefore will have a sharper penumbra, thus verifying the setup jaw and scanner orientation geometry. Similar analysis may be performed on scans where there is no change in setup but only a repeat, indicating that a ratio of unity (flat line) is expected, again a QA function that may be automated.

Figure 11:
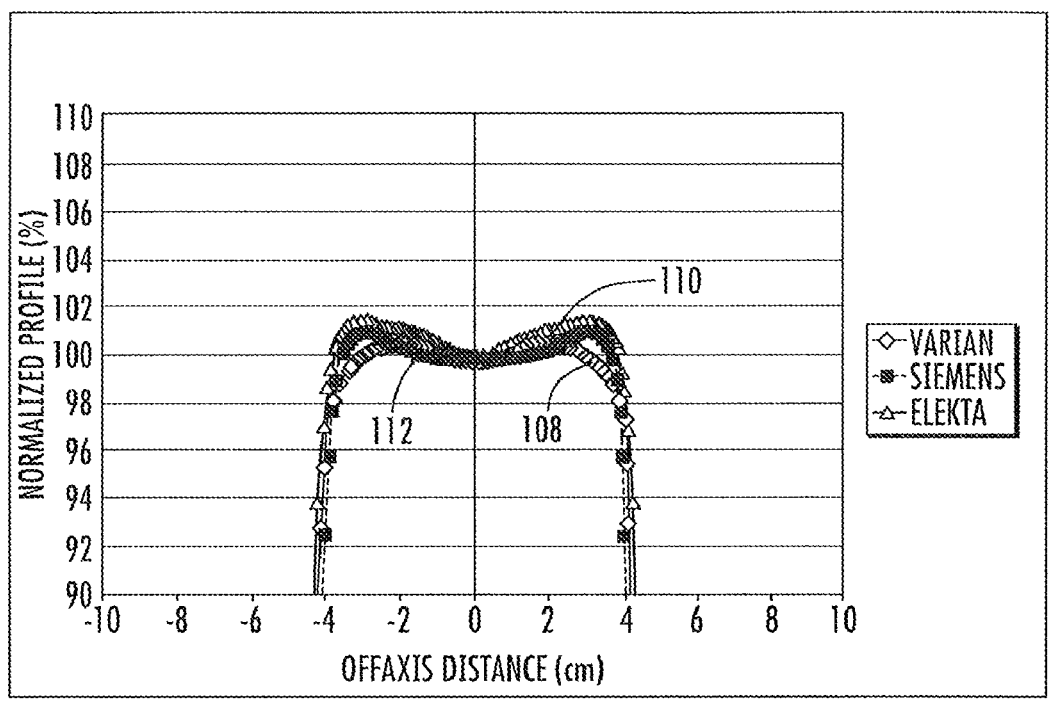
FIG. 11 illustrates in-line profile comparisons for 10 cm×10 cm field, 1.5 cm depth, zoom in-line (axial, IEC Y axis) on Varian, Siemens and Electa machines (90 SSD, Raw Symmetrized Scan Data)

By way of another example, and with reference to the data plot of FIG. 11, another overview of the QA method is illustrated as the profiles scanned on different LINAC's Varian[2], Elekta[10], and Siemens[11], with the scans being made in the same beam geometry (setup) and depth. The profile from the Varian 108, the profile from the Elekta 110 and the profile from Siemens 112 look similar until they are overlaid and zoomed in to examine the finer detail, where the differences in the flattening filters, a device in the LINAC to shape the raw X-ray beam, are clearly seen, producing an identity print of the of the three machines. These profile shapes should be characteristic to the manufacturer, i.e., this is one of the principle differences between machine makes, the other being the beam edge shape in the penumbra region as described with FIG. 10. Such measurements and analysis provide another QA check of the scanning and the LINAC when the profile is compared to a library of benchmark scans from known machine makes, or when comparing historical scan data that verifies clinical use. In this example, the ratios were not illustrated because a demonstration of the profile shapes of the three manufacturers would have been hidden, however for the same manufacturer but different machines, such a ratio would reveal the matching or non-matching characteristics of the LINACs.

Figure 12:
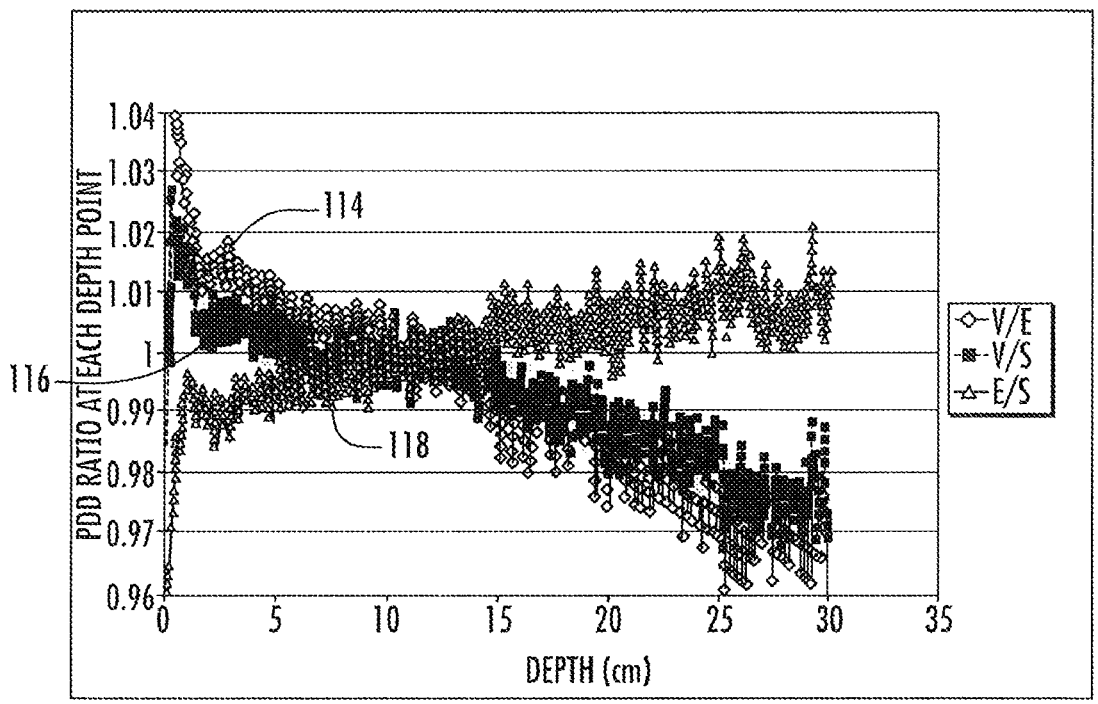
FIG. 12 illustrates a point normalization of 4 cm×4 cm PDD curves between Varian, Elekta and Siemens machines.

By way of yet another example, and with reference to the data plot of FIG. 12, another overview of the QA method is illustrated as the ratios of the percent depth dose (PDD, fractional depth dose FDD) curves scanned on different LINAC's Varian[2], Elekta[10], and Siemens[11], with the scans being made in the same beam geometry (setup). A comparison of machine PDD provides a convenient and quantitative method to compare the "beam matching" between machines. From each machine data, the PDD's were compared by taking point-to-point ratios. These ratio plots are for field sizes 4×4 cm. A linear regression fit between 3 cm and 30 cm on the 4×4 cm field size resulted in the following:
  a. VIE: y=−0.0018x+1.0176 R$^2$=0.9383 114
  b. VIS: y=−0.0011x+1.0098 R$^2$=0.8559 116
  c. E/S: y=0.0006x+0.9921 R$^2$=0.6903 118
The quality of the linear fit is expressed as R$^2$, with perfect being 1.00. The plots are reasonably linear in this small 4×4 cm field. The slope term is a statement of the beam matching, where two beams that are identical will have a PDD ratio that is unity throughout the depth, and a slope of zero without trend. From the values above, the machine ratios have slopes less than 0.2% from zero. The best matching is between Elekta and Siemens, with a 0.06% change in attenuation per cm; i.e., over a 30 cm depth range, the attenuation difference between beams is 1.8.

As earlier described with reference to FIG. 3, the water surface sensor 68 may be provided including an ultrasonic surface sensor or capacitive surface sensor having a sharp conductive point connected to electronic means of contact detection, that when mounted on the linear horizontal drive, measures the water surface at three or more non-collinear positions (a surface) by adjusting the vertical drive 32 until the surface 70 is located. The software may then analyze the level error of the three dimensional cylindrical scanning system with respect to the water surface and either instruct the operator to make level adjustments with leveling means that may include scaled adjustment controls, or adjust motorized leveling screws, or compensate for the level error with instructions to the three dimensional cylindrical scanning system control in such a way that keeps the radiation field sensor level (parallel) to the water surface.

To further aid the reader, the risks and possible mitigations of a cylindrical design are herein presented by way of example and may include:

Misalignment of the scan ring axis 24 to beam axis 78, as earlier described with reference to FIGS. 1 and 2: The scan ring axis may desirably be autoset to the beam axis with an additional hardware (ex: a small drive or axis adjustment device 76 on the detector mount 40 as earlier described with reference to FIG. 2). Alternatively, there may be provision in a ring axis mount that would allow for such adjustments. Beam axis alignment is critical in SRS fields below 2 cm diameter or square. In the present embodiment, there are two fine X-Y adjustments 120 in the lift table 72 that provide the alignment capability. The software analysis of two sets of two orthogonal scans, each set measured at two different depths along the beam axis, results in the determination of beam centers that define the collinear beam axis that result in the required adjustments which the user then performs before collecting clinical beam data. With scaled adjustment controls, these scale adjustments can be the output of the analysis whereby the operator makes a quantitative adjustment to align the ring axis to the beam axis or the software controller performs quantitative adjustment with motorized X and Y controls.

Inability to scan on an off axis chord: This may be a risk if the ring motor 44 is not part of the scan control, i.e., if the ring movement 22 does not have the precision to locate a detector to a precision of ~0.2 mm, then it cannot be used to drive the detector 38, in conjunction with the horizontal drive 26, on a chord for scanning. In the embodiment above described by way of example, the ring drive 20 has a precision of better than 0.1 mm and a hysteresis of 0.03 mm, which provides, along with the precision of the vertical and horizontal drives 32, 26, an accurate scanning mechanism through any X, Y, Z point in the water.

For example, asymmetric fields that are offset from the beam axis are chord scans in this cylindrical system when scanned profiles run through the offset "field" center and parallel to the linac axes (inplane or crossplane). This scan geometry is a chord offset to the center of the circle. TPS beam data do not call for chord tracing in asymmetric fields. However, chord tracing would be required if the penumbra profile at the MLC leaf end were required for leaves that are off central axis, beyond the reach of the detector motor. The present embodiment with the precision ring drive, along with the other two axes, enables any chord scanning as well as scanning between any two spatial locations that are defined within the scanning range of the three dimensional cylindrical scanning system. A shift in the X or Y direction can also enable scanning on a chord.

In this cylindrical geometry, any PDD can be ray traced (using the vertical and linear horizontal axis drives) after the ring is rotated to align the divergent ray parallel to the scanning arm. A PDD in an asymmetric off axis field is the most likely requirement of this geometry.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the claims supported by this disclosure.

REFERENCES CITED IN THE SPECIFICATION

1. Indra J. Das, Chee-Wai Cheng, Ronald J. Watts, Anders Ahnesjö, John Gibbons, X. Allen Li, Jessica Lowenstein, Raj K. Mitra, William E. Simon, and Timothy C. Zhu, "Accelerator beam data commissioning equipment and procedures: Report of the TG-106 of the Therapy Physics Committee of the AAPM", Med. Phys. 35 4186 (2008)
2. Varian Medical Systems, Palo Alto Calif.
3. PTW, Freiburg Germany
4. IBA Scanditronix Wellhofer, Schwarzenbruck, Germany
5. JF Dempsey, et al., "A Fourier analysis of IMRT dose grid resolution", Med Phys, 32, 380-388, 2005
6. Guanghua Yan, Christopher Fox, Chihray Liu, and Jonathan G. Li, "The extraction of true profiles for TPS commissioning and its impact on IMRT patient-specific QA", Med. Phys. 35 3661 (2008)
7. B. Fraass, K. Doppke, M. Hunt, G. Kutcher, George Starkschall, R. Stern, J. Van Dyke, "American Association of Physicists in Medicine Radiation Therapy Committee Task Group 53: Quality assurance for clinical radiotherapy treatment planning", Med. Phys. 25. 1773-1829, October 1998
8. W. Simon et al "LINAC Dosimetry: Benchmark Data Set Uncertainty", Med. Phys. 33 2118 SU-FF-T-311: (2006
9. Sun Nuclear Corporation, Melbourne Fla.
10. Elekta, Crawley, England
11. Siemens, Erlangen, Germany That which is claimed is:

1. A multiple axes scanning system for measuring radiation from a radiation source, the system comprising:
a processor having means for analysis and data storage;
a controller operable with the processor;
a ring drive operable with the controller for providing a rotational movement about a first axis responsive to a command therefrom;
a horizontal drive operable with the controller for providing horizontal movement along a second axis, the horizontal drive operable with the ring drive for receiving a rotational movement therefrom about the first axis;
a vertical drive operable with the controller for providing a vertical movement of the horizontal drive along a third axis responsive to a command therefrom; and
a radiation detector carried by the horizontal drive for receiving the horizontal movement therefrom, the radiation detector providing sensing signals to the processor for locations of the radiation detector orientated through at least one of circular, horizontal, and vertical movement along the first, second and third axes, respectively, as a result of the commands from the controller.

2. The system according to claim 1, wherein the ring drive comprises a circular gear, and wherein the controller comprises a first motor operable with the circular gear for providing the rotational movement.

3. The system according to claim 1, wherein the horizontal drive comprises a belt and pulley assembly driven by a second motor for moving the radiation detector towards and away from the first axis of the ring drive.

4. The system according to claim 1, wherein the vertical drive comprises a screw gear driven by a third motor mounted to the ring drive.

5. The system according to claim 1, further comprising an electrometer operable between the processor and the radiation detector.

6. The system according to claim 1, further comprising a reference detector operable at a fixed location for comparing the sensing signals of the radiation detector to the reference detector.

7. The system according to claim 1, further comprising a vessel dimensioned for movement of the radiation detector therein.

8. The system according to claim 7, further comprising an offset mount operable with the horizontal drive, wherein the radiation detector is carried by the offset mount, and wherein the offset mount is dimensioned for extending the radiation detector to one of at least proximate and against an inside wall surface of the vessel during a scanning movement of the radiation detector along the first, second and third axes.

9. The system according to claim 7, wherein the vessel comprises a cylindrical shape.

10. The system according to claim 7, further comprising a liquid carried within the vessel.

11. The system according to claim 10, further comprising a surface sensor operable with the liquid for determining a location of a surface of the liquid.

12. The system according to claim 11, wherein the surface sensor is carried by the horizontal drive, thus allowing measurements to be taken at multiple non-collinear positions by movement of the vertical drive for locating the surface of the liquid.

13. The system according to claim 12, further comprising analysis means operable with the processor, the analysis means calculating a level error of a three dimensional scanning with respect to the water surface for making level adjustments for maintaining the radiation detector generally parallel to the water surface.

14. The system according to claim 11, wherein the surface sensor comprises at least one of an ultrasonic sensor and a capacitive sensor.

15. The system according to claim 7, further comprising a table, wherein the table carries the vessel thereon.

16. The system according to claim 15, further comprising adjustment means operable with the table for providing a leveling and shifting thereof.

17. The system according to claim 1, further comprising an offset mount carried by the horizontal drive, wherein the radiation detector is carried by the offset mount, and wherein the offset mount is dimensioned for extending the detector beyond a circumferential path of the circular ring drive during horizontal movement of the radiation detector through movement by the horizontal drive.

18. The system according to claim 1, further comprising further an axis adjustment device operable with the radiation detector for providing an alignment of a scan ring axis of the ring drive to a beam axis from a radiation source.

19. The system according to claim 18, further comprising analysis means operable with the processor, the analysis means analyzing orthogonal scans of the radiation detector at different vertical locations along a beam axis for providing a beam center that defines a collinear beam axis resulting in an adjustment to be made for collecting clinical beam data.

20. The system according to claim 1, further comprising analysis means operable with the processor, the analysis means calculating at least one of:
  ratios of normalized orthogonal scanned beam profiles resulting in a value of radial homogeneity of a radiation detected by the radiation detector and providing a comparison of a penumbra shape characteristic to beam shapers such as jaw positions;
  ratios of percent depth dose curves, normalized at same depth, measured at different beam energies, resulting in values that trend up or down, depending upon actual beam energy, thereby providing comparison means with expected trend;
  ratios of normalized profiles measured with a similar beam geometry but measured at different times in a queuing process, resulting in values that should not change if no physical setup changes occurred, no physical operating conditions of the scanning system occurred, no changes in a radiation delivery occurred; and
  ratios of normalized scans that have a corresponding radiation source setup conditions that were measured in a reference set of radiation source measurements that are known to be desirable.

21. The system according to claim 1, further comprising profile analysis means operable with the processor, the profile analysis means determining beam penumbra from a scanned penumbra by a de-convolution process of a scanned detector response, wherein the de-convolution process uses a chamber spread function that is determined from data measured by scanning the radiation detector that exhibits penumbra spreading and another detector that does not exhibit significant penumbra spreading.

22. A radiation measurement system comprising:
  a controller;
  a ring drive having a command connection with the controller for providing a rotational movement about a first axis;
  a horizontal drive having a command connection with the controller, the horizontal drive operable along a second axis in a horizontal movement generally parallel to a diameter of the ring drive; and
  a radiation detector carried by the horizontal drive for the horizontal movement of the radiation detector.

23. The system according to claim 22, wherein the ring drive comprises a circular gear, and wherein the controller comprises a first motor operable with the circular gear for providing the rotational movement.

24. The system according to claim 22, wherein the horizontal drive comprises a belt and pulley assembly operable with a second motor for moving the radiation detector along a second axis toward and away from the first axis of the ring drive.

25. The system according to claim 22, further comprising a vertical drive having a command connection with the controller for providing a vertical movement along a third axis.

26. The system according to claim 25, wherein the vertical drive comprises a screw gear driven by a third motor mounted to the ring drive.

27. The system according to claim 22, further comprising a processor, wherein the controller and the radiation detector communicate with the processor for providing sensing signals to the processor for locations of the radiation detector orientated through movement by the drives.

28. The system according to claim 27, further comprising an electrometer operable between the processor and the radiation detector.

29. The system according to claim 22, further comprising a reference detector operable at a fixed location for comparing the sensing signal of the radiation detector to radiation signals from the reference detector.

30. The system according to claim 22, further comprising a vessel dimensioned for movement of the radiation detector therein.

31. The system according to claim 30, further comprising an offset mount operable with the horizontal drive, wherein the radiation detector is carried by the offset mount, and wherein the offset mount is dimensioned for extending the detector to at least one of proximate and against an inside wall surface of the vessel during movement of the radiation detector along the axes.

32. The system according to claim 22, wherein the radiation detector is operable with a liquid, and wherein the system further comprises a surface sensor operable for determining a location of a surface of the liquid.

33. The system according to claim 22, further comprising an offset mount carrying the radiation detector, wherein the offset mount is dimensioned for extending the radiation detector beyond a circumferential path of the ring drive during movement of the radiation detector along the second axis.

34. The system according to claim 33, wherein the radiation detector comprises multiple radiation detectors.

35. A radiation measurement scanning system comprising:
a controller:
a circular ring drive defined about a first axis;
a horizontal linear drive operable with at least one of the vertical linear drive and the circular ring drive for vertical movement of the horizontal linear drive thereby along a second axis;
a vertical linear drive operable along a third axis for movement of the horizontal drive therealong;
a radiation detector carried by the horizontal linear drive; and
at least one motor coupled to the drives, the at least one motor having a command connection with the controller for providing a movement of the radiation detector along at least one of the first, second and third axes, wherein the radiation detector provides sensing signals for locations of the radiation detector orientated through at least one of circular, vertical and horizontal movement thereof.

36. The system according to claim 35, wherein the circular ring drive comprises a circular gear, and wherein the controller comprises a first motor operable with the circular gear for providing a rotation thereof.

37. The system according to claim 35, wherein the horizontal linear drive comprises a belt and pulley assembly operable by a second motor for moving the radiation detector through and away from the first axis of the circular ring drive.

38. The system according to claim 35, wherein the vertical linear drive comprises a screw gear driven by a third motor mounted to the circular ring drive.

39. The system according to claim 35, further comprising an electrometer operable with the radiation detector.

40. The system according to claim 35, further comprising a reference detector operable at a fixed location for comparing the sensing signal from the radiation detector to radiation signals from the reference detector.

41. The system according to claim 35, further comprising a processor operable with the controller and the radiation detector.

42. The system according to claim 41, further comprising analysis means operable with the processor, the analysis means calculating at least one of:
ratios of normalized orthogonal scanned beam profiles resulting in a value of radial homogeneity of a radiation detected by the radiation detector and providing a comparison of a penumbra shape characteristic to beam shapers such as jaw positions;
ratios of percent depth dose curves, normalized at same depth, measured at different beam energies, resulting in values that trend up or down, depending upon actual beam energy, thereby providing comparison means with expected trend;
ratios of normalized profiles measured with a similar beam geometry but measured at different times in a queuing process, resulting in values that should not change if no physical setup changes occurred, no physical operating conditions of the scanning system occurred, no changes in a radiation delivery occurred; and
ratios of normalized scans that have a corresponding radiation source setup conditions that were measured in a reference set of radiation source measurements that are known to be desirable.

43. The system according to claim 41, further comprising profile analysis means operable with the processor, the profile analysis means determining beam penumbra from a scanned penumbra by a de-convolution process of a scanned detector response, wherein the de-convolution process uses a chamber spread function that is determined from data measured by scanning the radiation detector that exhibits penumbra spreading and another detector that does not exhibit significant penumbra spreading.

* * * * *